United States Patent [19]

Herrmann

[11] 4,065,363
[45] Dec. 27, 1977

[54] PROCESS FOR THE ELECTROMETRIC MEASUREMENT OF CYANIDE IONS IN SOLUTIONS CONTAINING METAL IONS

[75] Inventor: Gunther Herrmann, Furth, Germany

[73] Assignee: Photocircuits Division of Kollmorgen Corporation, Hartford, Conn.

[21] Appl. No.: 205,297

[22] Filed: Dec. 6, 1971

[30] Foreign Application Priority Data

Dec. 17, 1970 Germany .............................. 2064822

[51] Int. Cl.$^2$ ............................................ G01N 27/46
[52] U.S. Cl. ................................ 204/1 T; 204/195 M; 427/437; 96/60 R
[58] Field of Search ....................... 106/1; 117/130 E; 204/1 T, 195 M, 195 L

[56] References Cited

U.S. PATENT DOCUMENTS

| | | | |
|---|---|---|---|
| 3,337,350 | 8/1967 | Hata et al. ................................ | 106/1 |
| 3,615,737 | 10/1971 | Schneble et al. ......................... | 106/1 |
| 3,650,777 | 3/1972 | Schneble et al. ......................... | 106/1 |

OTHER PUBLICATIONS

"Ion Selective Electrodes", NBS Pub. 314, Nov. 1969, p. 371.
"Analytical Chem.", vol. 43, No. 12, Oct. 1971, pp. 1575–1581.
"Plating", July, 1971, pp. 686–693.
Orion Instruction Manual, "Cyanide Activity Electrode", 1967, pp. 1–16.

*Primary Examiner*—T. Tung
*Attorney, Agent, or Firm*—Morgan, Finnegan, Pine, Foley & Lee

[57] ABSTRACT

This invention is concerned with a novel process for the electrometric determination of the cyanide ion content of solutions comprising cyanide ion, a strong reducing agent and a metal ion.

1 Claim, No Drawings

PROCESS FOR THE ELECTROMETRIC MEASUREMENT OF CYANIDE IONS IN SOLUTIONS CONTAINING METAL IONS

BACKGROUND OF THE INVENTION

Process and specialized apparatus have been described in the prior art which have been specially adapted for the electrometric determination of the cyanide ion content of solutions thereof. Heretofore, it has not been possible, however, to apply this specialized apparatus to solutions containing cyanide ion, a strong reducing agent and a metal ion. This was due to the fact that the metal ion would be deposited on the electrode as the free metal and would eventually render the electrode inoperative. Applicant has provided a solution for this problem which is a novel method for measuring the cyanide ion content of metal ion containing solutions.

SUMMARY OF THE INVENTION

The invention provides a method of electrometrically measuring the cyanide content of solutions, containing cyanide ion, a metal ion such as silver or copper and a strong reducing agent such as formaldehyde.

It is an object of this invention to provide a method for electrometrically measuring the cyanide ion content of solutions such as are customarily employed in the photographics, electroless plating and other industrial processes.

This and other objects will become apparent from the detailed description.

DETAILED DESCRIPTION

Ion selective electrodes for use in the determination of the cyanide ion content of solutions are described in the literature and are commercially available. The membrane material of such special electrodes as a rule consists of AgCl, AgBr, Ags or AgCN. The system Ag/AgCl in KCl of a specific molarity, e.g., 0.01M, or Ag/AgBr in KBr, Ag/AgI for example, serves as the reference electrode. These type electrodes are also described in Ion Selective Electrodes, National Bureau of Standards Special Publication, 314, Issued November 1969, which is incorporated by reference.

The ion selective electrodes may be used in connection with a device for measuring potential differences such as an expanded scale pH meter or more preferably a specific ion meter of the type designed for use in measuring small differences in ion concentration. These instruments are commerically available.

The measuring procedure depends on the slow dissolving of the active membrane constituent; the cyanide ions present in the solution combine with the slightly soluble silver salts of the membrane surface for the measurement. This reaction proceeds as follows:

$$AgX + 2 CN^- \rightarrow Ag(CN)_2^- + X^-$$

The $X^-$ ions liberated in this reaction determine the activity of the silver ions at the membrane surface in accordance with the solubility product relation $$A_{Ag^+} = L/B \cdot a_{X^-}$$

in which L is the solubility product of the silver salt, B the stirring velocity and $a_{X^-}$ the activity of the $X^-$ ions. By substitution in the Nernst equation $$E = E_o + RT \cdot n^{-1} \cdot F^{-1} \cdot \ln 2L/B \, a_{CN^-}$$

or, after rearrangement, $$E = E_o + RT \cdot n^{-1} \cdot F^{-1} (\ln 2L/B - \ln a_{CN^-})$$

results. If the stirring velocity and the temperature are kept constant, $E_o$ and $\ln 2L \cdot B^{-1}$ are constant and $+RT \cdot n^{-1} \cdot F^{-1}$ can be set equal to a constant $K_1$.

Thus, for $$E = E_1 + RT \cdot n^{-1} \cdot F^{-1} \cdot \ln a_{CN^-}$$
or for: $\Delta E = E - E_1 \; E = K_1 \ln a_{CN^-}$ results. Hence, it follows that the direct measurement of cyanide ion concentration at constant stirring velocity and temperature is possible so far as no side reactions occur at the membrane in the solution to be measured.

At the appearance of such side reactions, however, the use of this measurement concept to determine cyanide ion concentration had hitherto proved unavailing in solutions that contain a strong reducing agent. The reducing agent leads to the formation of a metal, here a silver deposit on the membrane.

According to the process of the invention, the formation of such a metal deposit is prevented by providing a solution sample for use in the determination of the cyanide ion concentration which contains a complexing agent for the metal.

The complexing agent must be so chosen that it does not interfere with the test reaction. For example, triethylenetetramine, ethylenediaminetetraacetic acid, N',N',N,N-tetrakis-2(2-hydroxypropyl)ethylenediamine, citric acid, tartaric acid, 1,3-propanediamine, diethylenetriaminepentaacetic acid, Rochelle salt, mono-, di- and trisodium salts of n-hydroxy-ethylenediaminetetraacetic acid, nitrilotriacetic acid and its salts, triethanolamine, and cyclohexanediaminetetraacetic acid have proved to be suitable.

If metal ions which form complexes with the complexing agent are present in the bath solution specified for the concentration measurement, care must be taken, in accordance with the present invention that the complexing agent is added in an amount that leads to an excess of that required to complex the metal ions.

If bath solutions are to be measured for example, baths for autocatalytic metal deposition on sensitized surfaces, already contain a complexing agent for the metal ions along with a metal compound, care must be taken in accordance with the invention that the complexing agent be present in excess. If a separate complexing agent is added to such a solution, it is important that the sum of the complexing agents present must result in an excess in order to permit the undisturbed determination of the cyanide ion concentration according to the invention.

The following Examples are given by way of illustration and are in no way to be construed as limitations on the scope of the invention:

EXAMPLE I

An electrode supplied by Orion Research Incorporated, Cambridge, Mass. which is described as the Ionalyzer cyanide ion activity electrode, Model # 94-06-00 was employed to monitor the cyanide ion activity of the following electrodes copper bath:

| | | |
|---|---|---|
| Copper sulfate | 10. | g/l |
| Tetrasodium EDTA | 46. | g/l |

| | -continued | |
|---|---|---|
| Formaldehyde 37% | 4.0 | m/l |
| Sodium cyanide | 25. | mg/l |
| Gafac RE 610 | 0.25 | g/l |
| pH at 25° C | 12.4 | |

The use of the excess of the tetrasodium EDTA made possible the monitoring of the cyanide concentration.

EXAMPLE II

A cyanide ion content of the silver bath of the following formulation is also monitored by the technique of Example I:

| | g/l | moles/l |
|---|---|---|
| Silver nitrate | 1.7 | 0.010 |
| Sodium potassium tartrate | 4 | 0.014 |
| Sodium cyanide | 1.8 | 0.04 |
| Dimethylamine borane | 0.8 | 0.013 |

| | -continued | |
|---|---|---|
| | g/l | moles/l |
| Water qsad | 100.0 | |
| pH | 13.0 | |

Further variations in the application of the process of the invention will be readily understood by those skilled in the art, however, in each case it should be remembered that an excess of complexer must be employed.

What is claimed is:

1. A process for the determination of the cyanide ion content of a solution which comprises cyanide ions, a strong reducing agent, and a silver ion, said method comprising providing in said solution an amount of metal complexer in excess of that required to complex the silver ion; providing in contact with said solution a cyanide ion selective electrode that has connected thereto, direct reading potentiometric measurement means and, thereafter, determining from said direct reading potentiometric measurement means the cyanide ion concentration.

* * * * *